United States Patent [19]

Alexander et al.

[11] Patent Number: 5,135,744

[45] Date of Patent: Aug. 4, 1992

[54] PALATABLE SOLID PESTICIDAL COMPOSITIONS OF ETHYLENE AND VINYL ACETATE COPOLYMER

[75] Inventors: Samuel R. Alexander, Bay St. Louis, Mich.; Aref A. Aref, Hockessin, Del.; Malcolm S. Smith, Beaumont, Tex.

[73] Assignee: E. I. du Pont de Nemours and Company, Wilmington, Del.

[21] Appl. No.: 603,731

[22] Filed: Nov. 21, 1990

Related U.S. Application Data

[63] Continuation-in-part of Ser. No. 208,311, Jun. 17, 1988, abandoned.

[51] Int. Cl.⁵ .................... A01N 25/10; A61K 47/32; A61K 9/16; A01M 1/20
[52] U.S. Cl. ............................ 424/78.17; 424/409; 424/410; 424/84; 424/DIG. 8; 424/486; 424/501
[58] Field of Search ........... 424/410, 409, 84, DIG. 8, 424/DIG. 11, 78.17; 427/1; 43/124; 514/918–920

[56] References Cited

U.S. PATENT DOCUMENTS 4,237,113 12/1980 Cardarelli ...................... 424/78
4,741,904 5/1988 Smith et al. .................. 43/44.99

FOREIGN PATENT DOCUMENTS 2115698 9/1983 United Kingdom .

*Primary Examiner*—Thurman K. Page
*Assistant Examiner*—E. J. Webman

[57] ABSTRACT

The invention comprises compositions in solid form of ethylene/vinyl acetate copolymer with an effective amount of bioactive agent, a protein/carbohydrate-lipid source, 0 to 20% of an edible oil and optionally an attractant, dye, preservative, adversive agent and biomarker and the use, thereof, to control pests.

1 Claim, No Drawings

PALATABLE SOLID PESTICIDAL COMPOSITIONS OF ETHYLENE AND VINYL ACETATE COPOLYMER

RELATED APPLICATIONS

This is a continuation-in-part of U.S. Ser. No. 07/208,311 filed Jun 17, 1988, abandoned Jul. 6, 1989.

BACKGROUND OF THE INVENTION

The present invention relates to pesticidal compositions and their use to control pests and to treat wild animals. More specifically, the present invention relates to palatable pesticidal compositions comprising an ethylene/vinyl acetate copolymer, a bioactive agent, a protein/carbohydrate/lipid source and optionally various other additives.

U.S. Pat. No. 4,576,821 discloses the use of ethylene/vinyl acetate copolymers in fish and crustacean bait compositions consisting essentially of (a) from about 5 to about 50 weight % of the copolymer; (b) from about 45 to about 95 weight % of attractant selected from the group consisting of fish meal and powdered fish; and (c) from 0 to about 20 weight % fish oil.

U.S. Pat. No. 4,666,717 discloses the use of ethylene/vinyl acetate copolymers in fish and crustacean bait compositions consisting essentially of (a) from about 2 to about 50 weight % of the copolymer; (b) from about 45 to about 98 weight % of a plant-derived particulate attractant; and (c) from 0 to about 20 weight % of edible oil or molasses.

U.S. Ser. No. 024,171, filed Mar. 10, 1987, discloses the use of ethylene/vinyl acetate copolymer in fish and crustacean feed compositions consisting essentially of (a) from about 0.5 to about 10 weight % of the copolymer; (b) from about 75 to about 95 weight % of a nutrient medium selected from the group consisting of fish meal, crustacean meal, grain-derived products, plant-derived products, animal-derived products, and fish by-products; (c) from 0 to about 20 weight % of a lubricant selected from the group consisting of edible oil and fish solid solubles; (d) from 0 to about 10 weight % of a vitamin and mineral concentrate; and (e) from 0 to about 10 weight % of a preservative.

U.S. Pat. No. 4,237,113 discloses a slow-release insecticide polymer composition for distribution upon a non-water surface comprising (a) 100 parts by weight ethylene/vinyl acetate copolymer said copolymer having a weight average molecular weight of from about 40,000 to about 400,000 with the amount of ethylene in said copolymer ranging from about 60 to about 95 weight %; and (b) 0.2 to 40 parts by weight of a nonvolatile insecticide.

U.S. Pat. No. 4,237,114 discloses a composition for destroying aquatic pests over a period of time comprising (a) 100 parts by weight of a polymer matrix consisting of an ethylene/vinyl acetate copolymer, said ethylene/vinyl acetate copolymer ranging from about 60 to about 95% ethylene; (b) from about 25 to about 75 parts by weight per 100 parts of said matrix of a toxicant; and (c) from about 15 to about 70 parts by weight per 100 parts of matrix of a moderate to low solubility porosity inducing agent selected from the group consisting of a non-alkaline earth salt and non-alkaline earth oxide.

U.S. Pat. No. 4,299,613 discloses a controlled-release plant nutrient dispenser comprising (a) a uniformly dispersed admixture of a plant nutrient; (b) a porosigen; and (c) 100 parts by weight of a polymer matrix consisting of an ethylene/vinyl acetate copolymer the amount of weight of said ethylene consistuent ranging from about 60 to about 95 weight percent.

U.S. Pat. No. 4,166,111 discloses a composition for destroying aquatic pests over a period of time comprising (a) 100 parts by weight of a polymer matrix consisting essentially of an ethylene/vinyl acetate copolymer, the amount by weight of said ethylene constituent in said copolymer ranging from about 60 to about 92%; (b) a toxicant; and (c) from about 15 to about 70 parts by weight per 100 parts of said matrix of a porosity-inducing agent being an alkaline earth salt or alkaline earth oxide having a medium to low solubility in water.

U.S. Pat. No. 4,544,155 discloses a solid, controlled release, biologically active pesticide material delivery composition for release of the biologically active pesticide material over an extended period of time consisting essentially of (a) a solid solution of kraft lignin and a biodegradable water-insoluble organic polymer and (b) a pesticide.

EP-A-64,379 discloses a pesticidal composition characterized in that it comprises (a) a pesticide and (b) a polymer having a crystallinity of 0–30%, an effective glass transition temperature of from −15° to 50° C. with the weight ratio of the pesticide and polymer ranging from 40/60 to 99/1.

GB 2,115,698 discloses rodenticidal block bait compositions consisting essentially of (a) a brittle-hard polyvinyl acetate or copolymer of vinyl acetate and acrylic acid esters, methacrylic acid esters and/or acrylonitrile; (b) a foodstuff preparation; and (c) a rodenticidal poison.

Government regulations are moving rodent, roach and other household pest-killing compositions toward enclosed tamper-proof systems that prevent accidental contact by nontarget species. For example, rodent baits are now available in sealed containers with small openings that allow the rodent to enter, eat a portion of the bait and ultimately die. The compositions in use presently for rodent application are referred to as "paraffin block baits." They contain an attractant (grain, etc.), a binder (about 33% food grade paraffin) and a low level of active ingredient (warfarin, brodifacoum, etc.). The palatability and crumbly nature of these baits upon rodent feeding is marginal at best.

There is a need not only for a rodent pesticide that is safely usable but also other pesticidal compositions that do not have the shortcomings of the above prior art or have advantages thereover. There is also a need for pesticidal compositions that can be used to treat wild animals with vaccines or contraceptives.

SUMMARY OF THE INVENTION

This invention relates to a palatable pesticidal composition in solid form comprising based on the total composition
 (a) 0.5 to 33 weight % of ethylene/vinyl acetate copolymer with from 18 to 50 weight % vinyl acetate,
 (b) an effective amount of a bioactive agent, and
 (c) a protein/carbohydrate/lipid source providing the remaining weight.

Generally, the compositions of the invention can be advantageously used with one or more of the below listed optional ingredients:
 (d) from 0 to 20 weight % of edible oil, (e) optionally an attractant,
(f) optionally a dye,
(g) optionally a preservative,
(h) optionally an adversive agent, and
(i) optionally a biomarker, with
the amount of the aforesaid option ingredients identified in (e), (f), (g), (h) and (i) total 0–5% by weight based on the composition. However, even greater amounts can be used but do not improve the effectiveness of the composition.

The term "attractant" refers to a material or materials other than the protein/carbohydrate/lipid source which through smell or taste or both attract the pest to the composition and/or render it more appetizing. Nonlimiting examples include amino acids, pheromones, flavor enhancers and sugars.

Protein/carbohydrate/lipid sources include, but are not limited to, plant-derived materials such as grain, bran, processed grain products, forage products, farm products, fish meal, fish products or combinations thereof. Generally, the amount of protein/carbohydrate/lipid material in the compositions of the invention can vary widely. Generally about 67 to 99% by weight are used depending on the pest.

Edible oils include, but are not limited to mineral, plant derived or fish oils or combinations thereof. They are optionally required as a lubricant, depending on the composition, for ease of processing.

The term "bioactive agent" refers to a toxicant or therapeutic agent. Nonlimiting examples of toxicants include insecticides, molluscicides and rodenticides. Nonlimiting examples of therapeutic agents include oral vaccines and oral contraceptives. An effective amount refers to the dose resulting in fatality in the case of a toxicant upon consumption of the composition by the pest or the dose required to produce the desired pharmacologic effect upon consumption in the case of a therapeutic agent. Such quantities will thus be quite dependent upon the nature of the toxicant or therapeutic agent, the pest, and the amount of the composition expected to be consumed. Generally, at least 0.001% by weight of the bioactive agent is required based on the weight of the composition. Generally, more than 10% by weight of the composition of bioactive agent can be used but offers no advantage over amounts in the range of 0.001% –10%.

The term "preservative" refers to commercial food preservatives, insecticides, antioxidants, antimold, antimildew or antifungal agents utilized to prevent spoiling of the protein/carbohydrate/lipid food material.

The term "adversive agent" refers to a material or materials added to prevent consumption or digestion of the composition by a non-target organism. Nonlimiting examples include bittering agents, emetics and repellents.

The term "biomarker" refers to an agent which once consumed by the pest can be detected after extended periods of time by analytical means or upon a pathological examination.

The term "pest" includes any vertebrate or invertebrate organism which injures man, his property or his environment or which annoys him. Such organisms include principally certain insects, acarids and small animals. In the context of this application, an unvaccinated wild animal which can contract and spread disease is included in the scope of the term "pest."

The preferred pesticidal compositions are:

1. The compositions of the invention wherein the copolymer is 1 to 33 weight % with 25 to 40 weight % vinyl acetate.
2. The compositions of Preferred 1 wherein the copolymer is from 31 to 35 weight % vinyl acetate.
3. The compositions of the invention wherein the edible oil is 0 to 10 weight %.
4. The compositions of the invention wherein the bioactive agent is 0.001 to 10 weight %.
5. The compositions of Preferred 4 wherein the bioactive agent is 0.005 to 10 weight %.
6. The compositions of the invention wherein the copolymer is 5 to 33 weight % and the target pest is a vertebrate pest.
7. The compositions of Preferred 6 wherein the copolymer is 15 to 25 weight %.
8. The compositions of Preferred 7 in the form of a block.
9. The compositions of Preferred 7 wherein the vertebrate pest is a rodent and the bioactive agent is a rodenticide.
10. The compositions of the invention wherein the copolymer is 1 to 5 weight % and the target pest is a vertebrate pest.
11. The compositions of Preferred 10 in the form of pellets.
12. The compositions of Preferred 10 wherein the vertebrate pest is a rodent and the bioactive agent is a rodenticide.
13. The compositions of the invention wherein the copolymer is 2 to 20 weight % and the target pest is a vertebrate pest.
14. The compositions of Preferred 13 wherein the copolymer is 3 to 15 weight %.
15. The compositions of Preferred 14 in the form of a cavity containing block.
16. The compositions of Preferred 14 wherein the vertebrate pest is selected from the group consisting of racoons, foxes or skunks, and the bioactive agent is an oral rabies vaccine.
17. The compositions of Preferred 14 wherein the vertebrate pests are deer and the bioactive agent is an oral contraceptive.
18. The compositions of the invention wherein the copolymer is 2 to 20 weight % and the target pest is an invertebrate pest.
19. The compositions of Preferred 18 wherein the copolymer is 3 to 15 weight %.
20. The compositions of Preferred 19 in the form of pellets.
21. The compositions of Preferred 19 wherein the invertebrate pest is an insect and the bioactive agent is an insecticide.
22. The compositions of Preferred 19 wherein the invertebrate pest is a mollusc and the bioactive agent is a molluscicide.

The pesticidal compositions of the invention are useful in the control or elimination of pests from the locus of application of the compositions. The invention is therefore also directed to a method of controlling pests, said method comprising the use of the pesticidal compositions of the invention by locating the composition in places where control is to be effected such as the habitat of the pest.

DETAILED DESCRIPTION OF THE INVENTION

The compositions of this invention are prepared in any commercial extrusion equipment cabable of (1) melting the ethylene/vinyl acetate copolymer, a minimum of about 80° C., and (2) once molten, of mixing the polymer in an intimate fashion with the other ingredients which consist of natural grains, animal products, etc., in combination with an active ingredient and optionally various other materials to uniformly distribute the polymer over these ingredients to maximize the structural intregity of the final mix. Examples of such extrusion equipment are polyethylene type extruders with mixing devices, food processing extruders (Wenger) and pellet mill extruders such as the California Pellet Mill.

Preparation of the blend for extrusion is accomplished by intimately mixing the components of the blend conveniently in the dry state, by any one of several methods, e.g., drum tumbling, ribbon blender, etc. The components may be in powder form or pellets for blending.

The compositions of the invention may also be prepared by methods other than extrusion, e.g., by molding. However, the most efficient use of the copolymer of the invention is by the disclosed extrusion method.

Ethylene/vinyl acetate copolymers utilized in the compositions of the invention are available commercially from E. I. Du Pont de Nemours and Company, Inc., Wilmington, Del., under the trademark Elvax® in the form of pellets and powders.

U.S. Pat. Nos. 2,396,920 and 2,414,311 and German Patent 650,038 disclose details regarding the synthesis of ethylene/vinyl acetate copolymers of the invention. Re 32,325 discloses details of the handling of such polymers.

The copolymers of the invention permit high loading with respect to the other components of the composition thus allowing the use of a minimum amount of the copolymer, even as low as 0.5% while still affording some degree of physical integrity to the composition.

Processability of the copolymer at less than 110° C. enables one to avoid problems associated with thermal stability and water content of the ingredients. Such problems include thermal decomposition of active ingredient and formation of steam pockets caused by dehydration of the food material during extrusion at temperatures above 110° C. As the copolymer is soft and chewy in the ranges of the present invention, it does not adversely affect palatability of the composition to the pests.

The form the composition takes is dictated by the end-use application and the method of presentation of the final material. Shape extrusion of the composition once properly heated and mixed is an ideal method of producing a variety of forms. For example, blocks or pellets of any diameter limited by the extrusion equipment can be readily produced and cut at any desired length. Pellets ranging in diameter from 1/32" to blocks with diameters of 2" are readily made.

A pellet is any configuration, e.g., cylindrical, circular or triangular that is of a size such that 100 pellets weigh less than 10 grams.

A block is any configuration, e.g., cylindrical or otherwise, such that 1 block weighs more than 10 grams.

For some applications it may be more convenient for the solid form of the compositions of the invention to have a cavity. Thus, the extrusion process can be adapted so that a, e.g., 5/16-inch diameter rod is present in the middle of the extrusion die to produce the cavity. The bioactive agent can then be added in such cases to the cavity after extrusion. The cavity, after the bioactive agent is added, is sealed, e.g., by the use of paraffin wax. For example, in applications where the composition is a carrier for a thereuputic agent, the cavity can be used to hold a vaccine.

The copolymer content of the compositions of the present invention and their final forms will vary with the nature of the pest, the environment where the composition is expected to be effective and the requisite lifetime and methods of handling and application. For example, for smaller pests (i.e. insects, snails, slugs) pellets are well suited for distribution and treatment over large areas. In areas where non-pests may have access to the compositions, resistance to crumbling during contact with the pest is advantageous in order to reduce contamination of the habitat to a minimum. If a composition is to be used in an open outside environment, resistance to weathering (i.e. rain, etc.) may be desirable. For aerial application, the composition must have sufficient structural stability to withstand the fall and the form must have sufficient weight to penetrate bushes, etc., to contact the ground. With respect to handling (i.e. packaging, etc.) resistance to abrasion is desirable to prevent the formation of fines and dusts.

In general, the higher the copolymer content of the composition, the greater the structural integrity, resistance to abrasion and crumbling and the higher the weatherability.

Various bioactive agents which can be used in the compositions of the invention include but are not limited to rodenticides, molluscicides, insecticides, oral vaccines and oral contraceptives.

Rodenticides are materials used primarily for the control of rodents (rats, mice, etc.,) and related animals (such as rabbits). Representative examples of rodenticides are as follows: coumarins, indandiones, organochlorines, botanicals, organophosphates, pyriminilureas and inorganics. Nonlimiting examples of these rodenticides include the following:

arsenic trioxide (10% by weight of the composition)
    glycerol difluorohydrin--1,3-difluoro-2-propanol barium carbonate
sodium cyanide or fluoroacetate
thallous sulfate, nitrate or acetate
fluoroacetamide (0.2%)
glycerol chlorofluorohydrin -- 1-chloro-3-fluoro-2-propanol
thiosemicarbazide
bisthiosemi--1,1'-methylene di(thiosemicarbozide) (0.5-2%)
α-chlorohydrin--3-chloro-1,2-propanediol (1%)
phosacetim--
    -0,0-bis(4-chlorophenyl)-N-acetimidoylphosphor amidothioate
promurit--3,4-dichlorobenzenediazothiocarbamid diethyl stilbesterol
α-fluoro-p-bromoacetanilide
bromethalin--α,α, α-trifluoro-N-methyl-4,6-dinitro-N-(2,4,6-tribromophenyl)-o-toluidine (0.15%)
2,2-bis(4-fluoroethoxyphenyl)propane
2-valeryl-1,3-indandione
2-isovaleryl-1,3-indandione
pindone--pivalyl-1,3-indandione (0.5%)

diphacinone--
  -[2-diphenylacetyl-1,3-indandione](0.005–2.0%)
chlorophacinone--
  -2-[(p-chlorophenyl)phenylacetyl]-1,3-indandione (0.005–0.0075%)
rodione--2-(1-naphthyl)-1,3-indandione
antu--α-naphthylthiourea (1–3%)
cholecalciferol (0.75%)
calciferol (1%)
estranediol
estranol
mestranol
chlorinated ethyl furoate
chloralose--
  -(R)-1,2,-0-(2,2,2-trichloroethylidene)-α-0-glucofuranose (4%)
flupropadine--
  -4-t-butyl-1-[3-[3,5-bis(trifluoromethyl)phenyl]-2-propynyl]piperidine
pyriminil--1-(3-pyridylmethyl)-3-(4-nitrophenyl)-urea
crimidine--
  -2-chloro-4-dimethylamino-6-methylpyrimidine
tretamine--2,4-tris(1-aziridinyl)-s-triazine
silatrane
melitoxin
warfarin--3-(α-acetonylbenzyl)-4-hydroxycoumarin (0.5%–1%)
coumachlor--
  -3-(α-acetonyl-4-chlorobenzyl)-4-hydroxycoumarin (0.03–0.04%)
coumafuryl--3-α-acetonylfurfuryl)-4-hydroxycoumarin 0.25–0.50%)
coumatetralyl--
  -4-hydroxy-3-(1,2,3,4-tetrahydro-1-naphthalenyl)-2H-1-benzopyran-2-one 0.0375%)
difenacoum--
  -3-(3-1,1'-biphenyl-4-yl-1,2,3,4-tetrahydro-1-naphthylenyl)-4-hydroxy-2H-1-benzopyran-2-one (0.005%)
brodifacoum--
  -3-[3-(4'-bromo[1,1'-biphenyl]-4-yl)-1,2,3,4-tetrahydro-1-naphthalenyl]-4-hydroxy-2H-1-benzopyran-2-one (0.005%)
bromodiolone--
  -3-[3-(4'-bromo(1,1'-biphenyl]-4-yl)-3-hydroxy-1-phenylpropyl]-4-hydroxy-2H-1-benzopyran-2-one (0.005–2%)
flocumafen--
  -4-hydroxy-3-[1,2,3,4-tetrahydro-3-[4-(4-trifluoromethylbenzyloxy)phenyl]-1-naphthyl] coumarin (0.005%)
difethialone--3-[3-4 -bromo-4-biphenylyl)-1,2,3,4-tetrahydro-1-naphthyl]-4-hydoxy-2H-benzothiopyran-2-0
aminopterin--
  -N-[4-(2,4-diamino-6-pteridinylmethylamino)benzoyl] glutamic acid
norbormide--
  -5-(α-hydroxy-α-2-pyridylbenzyl)-7-(α-2-pyridylbenzylidene)-5-norbornene-2,3-dicarboximide (0.5–1%)
endrin--(1R, 4S, 5R, 8S)-1,2,3,4,10,10-hexachloro-1,4,4α, 5, 6, 7, 8, 8α-octahydro-6,7-epoxy-1,4,5,8-dimethanonaphthalene
tetramine
scillirocide--3β, 6β-6-acetyloxy-3-(β-D-glucopyranosyloxy)-8,14-dihydroxybufa-4,20,22-trienolide
strychnine (0.5–1%)
chloro-p-toluidine hydrochloride Molluscicides are materials used primarily for the control of slugs and snails which are crop and garden pests. Representative examples of molluscicides include the following:
cupric sulfate pentahydrate
cupric stearate
aluminum sulfate
metaldehyde--tetramethyl-1,3,5,7-tetoxocane (5% by weight of the composition)
dichloral urea--
  -1,3-bis(2,2,2-trichloro-1-hydroxyethyl)urea
mexacarbate--
  -4-dimethylamino-3,5-xylyl-N-methylcarbamate
methiocarb--3,5-dimethyl-4-(methylthio)phenylmethyl carbamate (4%)
niclosamide--
  -5-chloro-N-(2-chloro-4-nitrophenyl)-2-hydroxybenzamide (5%)
TBS--
  -N-(4-bromophenyl)-2-hydroxy-3,5-dibromobenzamide
N-isobutyl-N-triphenylmethylamine
trifenmorph--N-tritylmorpholine
isopimpinellin
2,6-dibromo-4-(4-nitrophenylazo)phenol Insecticides are materials used in the control of insects and have been classified as follows: organochlorines, organophosphates, organosulfurs, carbamates, formamidines, thiocyanates, dinitrophenols, organotins. botanicals synthetic pyrethroids, inorganics and microbials. Representative examples include the following:
allethrin--(RS)-3-allyl-2-methyl-4-oxocylcopent-2-enyl (1RS)-cis/trans chrysanthemate
ammonium fluosilicate
arsenic trioxide
avermectin B1
bacillus thuringiensis
borax--sodium tetraborate decahydrate
boric acid
calcium arsenate
cabaryl--1-naphthyl-N-methylcarbamate
carbofuran--2,3-dihydro-2,2-dimethyl-7-benzofuranyl methylcarbamate
chloropyrifos--O,O-diethyl O-(3,5,6-trichloro-2-pyridyl)-phosphorothioate
rotenone
diazinon--O,O-diethyl O-2-isopropyl-6-methylpyrimidin-4-yl-phosphorothioate
dimethoate--O,O-dimethyl S-(N-methylcarbamoylmethyl)phosphorodithioate
trichlorfon--dimethyl-2,2,2-trichloro-1-hydroxyethyl phosphonate (1% by weight of the composition)
monocrotophos--
  -dimethyl(E)-1-methyl-2-(methylcarbamoyl)vinylphosphate
fenoxycarb--ethyl 2-(4-phenoxyphenoxy)ethylcarbamate (1–5%)
propoxur--2-isopropoxyphenyl methylcarbamate
benzene hexachloride--
  -1,2,3,4,5,6-hexachlorocyclohexane
malathion--
  -diethyl(dimethoxyphosphinothioylthio)succinate
methomyl--S-methyl N-(methylcarbamoyloxy)thioacetimidate (1%)
methoprene--isopropyl (E,E)-(RS)-11-methoxy-3,7,11-trimethyldodeca-2,4-dienoate methiocarb-4-methylthio-3,5-xylylmethylcarbonate (4%)
mexacarbate--4-dimethylamino-3 5-xylylmethylcarbamate
naled--1,2-dibromo-2,2-dichloroethyl dimethyl phosphate nosema locustae (0.05%)
N-(2-ethylhexyl)-8,9,10-trinorborn-5-ene-2,3-dicarboximide
parathion--0,0-diethyl 0-4-nitrophenylphosphorothioate
permethrin--3-phenoxybenzyl (1RS,3RS;1RS,3SR)-3-(2,2 -dichlorovinyl)-2,2-dimethylcyclopropane carboxylate
pyrethrin I--(Z)-(S)-2-methyl-4-oxo-3(penta-2,4-dienyl)cyclopent-2-enyl (1R,3R)-2,2-dimethyl-3-(2-methylprop-1-enyl)cyclopropanecarboxylate
resmethrin--5-benzyl-3-furylmethyl (1RS,3RS;1RS,3SR) -2,2-dimethyl-3-(2-methylprop-1-enyl)cyclopropanecarboxylate
fenchlorphos--0,0-dimethyl 0-2,4,5-trichlorophenyl phosphorothioate
ryanodine--(2S, 3S, 4R, 4aS, 5S, 5aS, 8S, 9R, 9aR, 9bR)-2,3,4a,5a,9,9b-hexahydro-3-isopropyl-2a,5,8-trimethylperhydro-2,5-methanobenzo[1,2]-pentalenol[1,6-bc]furan-4-yl pyrrole-2-carboxylate
sodium arsenate
sodium fluoride
sodium fluosilicate--sodium hexafluorosilicate (10%)
toxaphene--67-69% chlorinated camphenes
dichlorvos--2,2-dichlorovinyl dimethyl phosphate
2-nitromethylene-tetrahydro-2H-1,3-thiazine
3-formyl-2-nitromethylene-tetrahydro-2H-1,3-thiazine Oral vaccines which can be used in the compositions of the invention include, but are not limited to, oral wildlife rabies vaccines for the immunization of wild animals. Such a vaccine for the immunization of raccoons is described by C. E. Rupprecht, B. Dietzchold, H. Koprowski and D. H. Johnston in *Vaccines* '87, 1987, pages 389-392.

Also included are oral vaccines for the treatment and control of deer anthrax.

Oral contraceptives which can be used in the composition of the present invention include, but are not limited to, oral contraceptives for mammals such as diethyl stilbestrol, mestranol and mibolerone, as described in J. D. Harder and T. J. Peterle, L; J. Wildl. Manage. 38(2), 183-196, and by D. Lednicer and L. A. Mitscher, "The Organic Chemistry of Drug Synthesis", Vol. 2, p. 144, Wiley, New York, 1980.

Attractants include, but are not limited to, food lures and chemical lures. Representative examples of food lures include the following:
amino acids and their derivatives
sugars
sugar syrups
ethylene methylphenylglycidate
acetophenone
amyl acetate
bitter almond
cinnamon
clove
coffee
fenugreek
isoamyl acetate
vanillin Chemical lures include, but are not limited to pheromones; representative examples of which include the following:
cyclopentadecatriene
decatriene
japonilure--4-(decen-1-yl)-butyrolactone
dimethyl-5-ethyl-6,8-dioxabicyclo(3.2.1)octane
DMCHE--dimethylcyclohexylidene ethanol
DMCHA--dimethylcyclohexylidene acetaldehyde
(Z)-9-dodecenyl acetate
(E)-9-dedecenyl acetate
orfamone--(Z)-8-dodecenyl acetate
disparlure--(Z)-7,8-epoxy-2-methyloctadiene
eugenol
(Z)-11-hexadecenal
gossyplure--(Z,Z)-7,11-hexadecadienyl acetate
limonene
grandisol--cis-methyl-2-(1-methylethenyl)cyclobutane ethanol
sulcatol--6 methyl-5-hepten-2-ol
geraniol
periplanone B
phenylethyl propionate
pinene
muscalure--(Z)-9-tricosene Protein/carbohydrate/lipid source includes, but is not limited to, plant-derived materials such as grain, bran, processed grain products, forage products, farm products, fish meal, fish products or combinations thereof.

Representative examples of the protein/carbohydrate/lipid source include fish meal, powdered fish, crab or other crustacean meal, meat scraps, milk solids, blood meal, grain flour (wheat flour, corn flour, etc.), wheat middlings, wheat bran, soybean meal, corn meal, corn gluten meal, sugar, molasses, algae meal, dried yeast, beans, rice, cottonseed and numerous animal and plant by-products well-known to one skilled in the art or mixtures thereof.

Representative examples of preservatives include the following:
benzoic acids, esters and salts
formaldehyde
sodium acetate
ascorbyl palmitate
proprionic acids, esters and salts
sorbic acid and sodium salt
1,2-benzisothiazolin-3-one (Proxel)
1,3-butylene glycol dimethylacrylate
methyl p-hydroxybenzoate
paraformaldehyde
sodium 0-phenylphenate
ethoxyquin A representative example of an adversive agent which is a bittering agent is denatonium benzoate (Bitrex), (0.001-0.03% by weight of the composition).

Representative examples of biomarkers include tetracycline, oxytetracycline and iophenoxic acid.

Representative examples of edible oils include fish oil, peanut oil, cotton seed oil, corn oil, molasses, mineral oil or fish solid solubles.

The dye may be selected from any of the group of commercial food dyes. Representative examples include the following:
FD&C Blue No. 1
Rhodamine B
Tartrazine (FD&C Yellow No.5)
D&C Green No. 6
D&C Red No. 17
D&C Violet No. 2
Methyl Violet 2B Malachite Green
Monolite Green Gn It should be recognized that various bioactive agents can also be used in combination with one another, for example, the use of a mixture of several insecticides as the toxicant. In addition, when the bioactive agent is a pyrethroid insecticide, a pyrethroid synergist may be added to the composition to increase the toxicant's effectiveness. The use and identity of pyrethroid synergists (e.g. piperonyl butoxide) are well known to one skilled in the art.

The following examples which further illustrate the invention are not to be construed as limiting the scope of the invention. The Elvax ® 150, utilized in the examples, is a copolymer of 31-35% by weight of vinyl acetate and 69-65% by weight of ethylene based on the weight of the copolymer. Mixtures of vaccines and contraceptives may also be used.

Rodent formulations are prepared as follows:

EXAMPLE 1

Elvax ® 150 (1 kg, 30 mesh powder), mineral oil (300 g), 4-hydroxy-3-(3-oxo-1-phenylbutyl)coumarin (2.5 g) and rat diet (8.69 kg.) consisting of 65% by weight cornmeal (whole yellow ground corn),
25% by weight rolled oat groats,
5% sugar (10X powdered) and
5% corn oil (Mazola)

are uniformly dry-blended by tumbling for about 7 minutes. The blended composition is fed to a 2.5 inch (63.5 mm) diameter extruder with the screen pack and breaker plate removed. The screw is rapid compression with a 20.6/1 L/D ratio and a mixing torpedo on the end of the screw. The melt temperature ranges from 80° C. to 110° C. Blocks are prepared with a diameter of 1.5 inches and a thickness of 0.5 to 0.75 inches.

EXAMPLE 2

Blocks are prepared as described in Example 1 from a blended composition of Elvax ® 150 (1.5 kg, 30 mesh powder), mineral oil (300 g), 4-hydroxy-3-(3-oxo-1-phenylbutyl)coumarin (2.5 g) and rat diet (8.19 kg).

EXAMPLE 3

Blocks are prepared as described in Example 1 from a blended composition of Elvax ® 150 (2 kg, 30 mesh powder), mineral oil (300 g), 4-hydroxy-3-(3-oxo-1-phenylbutyl)coumarin (2.5 g) and rat diet (7.69 kg).

EXAMPLE 4

Blocks are prepared as described in Example 1 from a blended composition of Elvax ® 150 (2.5 kg, 30 mesh powder), mineral oil (300 g), 4-hydroxy-3-(3-oxo-1-phenylbutyl)coumarin (2.5 g) and rat diet (7.19 kg).

EXAMPLE 5

Blocks are prepared as described in Example 1 from a blended composition of Elvax ® 150 (3.3 kg, 30 mesh powder), mineral oil (300 g), 4-hydroxy-3-(3-oxo-1-phenylbutyl)coumarin (2.5 g) and rat diet (6.39 kg).

Raccoon Formulations are Prepared as Follows:

EXAMPLE 6

A composition is blended as described in Example 1 from Elvax ® 150 (0.75 kg, 30 mesh powder), fish oil (1.5 kg), molasses (0.5 kg) and fish meal (7.25 kg). Cylindrical blocks 1 inch in diameter by 2 inches with a hole 5/16 inches in diameter (using a die with a 5/16-inch rod) forming a cavity in the center are prepared with each block weighing approximately 15 g. Oral rabies vaccine (1.ml with a titer of $10^7$-$10^8$ pfu/ml) as described by C. E. Rupprecht, et al., *Vaccines '87*, pages 389-392, is placed in each of the cavities and the openings sealed with paraffin wax.

EXAMPLE 7

Blocks are prepared as described in Example 6 from a blended composition of Elvax ® 150 (1 kg, 30 mesh powder), fish oil (1.5 kg), molasses (0.5 kg) and fish meal (7 kg) and filled with vaccine (1 ml, titer of $10^7$-$10^8$ pfu/ml).

EXAMPLE 8

Blocks are prepared as described in Example 6 from a blended composition of Elvax ®150 (1.5 kg, 30 mesh powder), fish oil (1.5 kg), molasses (0.5 kg) and fish meal (6.5 kg) and filled with vaccine (1 ml, titer of $10^7$-$10^8$ pfu/ml).

EXAMPLE 9

Blocks are prepared as described in Example 7 from a blended composition of Elvax ® 150 (2 kg, 30 mesh powder), fish oil (1.5 kg), molasses (0.5 kg) and fish meal (6 kg) and filled with vaccine (1 ml, titer of $10^7$-$10^8$ pfu/ml)

Mole-cricket Formulations are Prepared as Follows:

EXAMPLE 10

A blended composition is prepared as described in Example 1 from Elvax ® 150 (1.25 lb, 30 mesh powder), vegetable oil (3 lb.), diethyl (dimethoxyphosphinothioylthio) succinate (1.25 lb.) and corn meal (19.5 lb.) and extruded as cylindrical pellets ⅛-inch in diameter by ½-inch.

EXAMPLE 11

Pellets are prepared as described in Example 10 from a blended composition of Elvax ® 150 (2.5 lb, 30 mesh powder), vegetable oil (3 lb.), diethyl (dimethoxyphosphinothioylthio)succinate (1.26 lb) and corn meal (18.3 lb.)

EXAMPLE 12

Pellets are prepared as described in Example 10 from a blended composition of Elvax ® 150 (3.75 lb., 30 mesh powder), vegetable oil (3 lb.), diethyl (dimethoxyphosphinothioylthio)succinate (1.25 lb.) and corn meal (17 lb.).

EXAMPLE 13

Pellets are prepared as described in Example 10 from a blended composition of Elvax ® 150 (1.25 lb., 30 mesh powder), vegetable oil (3 lb.), diethyl (dimethoxyphosphinothioylthio)succinate (1.25 lb.), corn meal (19.5 lb.) and FD&C Blue No. 1 (28 g).

EXAMPLE 14

Pellets are prepared as described in Example 10 from Elvax ® 150 (2.5 lb., 30 mesh powder), vegetable oil (3 lb.), diethyl (dimethoxyphosphino-thioylthio)succinate (1.25 lb.), corn meal (18.3 lb.) and FD&C Blue No. 1 (28 g).

Slug Formulations Were Prepared as Follows:

EXAMPLE 15

The dry ingredients of the following composition were added to a double-cone blender and the vegetable oil was sprayed onto the tumbling mass for a total final weight of 50 lbs.:

| Component | % Wgt. |
|---|---|
| methomyl | 0.5 |
| Elvax ® 150 (30 mesh powder) | 10 |
| sucrose | 2.5 |
| Proxel GLX (1,2-benziso-thiazolin-3-one) | 0.1 |
| FD&C Blue No. 1 | 0.25 |
| Wheat middlings | 76.65 |
| Vegetable oil | 10 |

Blending was continued for an additional 15 minutes to insure a uniform mixture. The material was then extruded at temperatures between 80° and 100° C. using a Hartig 2-inch single screw extruder fitted with a 48-inch screw (length-to-diameter ratio of 24) and a 2-hole, ⅛ inch diameter faceplate die. The cooled extrudate was cut, and classified to a rough size of ¼-length.

EXAMPLES 16 AND 17

Pellets were prepared as described in Example 15 from 50 lbs. of a blended composition of the following ingredients;

| | % Weight | |
|---|---|---|
| Component | Example 16 | Example 17 |
| methomyl | 0.5 | 0.5 |
| Elvax ® 150 (30 mesh powder) | 12 | 15 |
| sucrose | 2.5 | 2.5 |
| Proxel GLX | 0.1 | 0.1 |
| FD&C Blue No. 1 | 0.25 | 0.25 |
| Wheat middlings | 76.65 | 73.65 |
| Vegetable oil | 8 | 8 |

EXAMPLES 18 AND 19

Pellets were prepared as described in Example 19 from 50 lbs. of a blended composition of the following ingredients.

| | % Weight | |
|---|---|---|
| Component | Example 18 | Example 19 |
| methiocarb | 5 | 5 |
| Elvax ® 150 (30 mesh powder) | 10 | 15 |
| sucrose | 2.5 | 2.5 |
| Proxel GLX | 0.2 | 0.2 |
| FD&C Blue No. 1 | 0.25 | 0.25 |
| Wheat middlings | 72.05 | 69.00 |
| Vegetable oil | 10 | 8 |

UTILITY

The palatable compositions of the invention are useful for the control of a variety of vertebrate and invertebrate pests. The bioactive agent can be a toxicant such as a rodenticide such that the composition can be utilized to control rodents, an insecticide or acaricide such that the composition can be utilized to control mites, ticks, spiders, lice, leafrollers, leafminers, earwigs, fleas, thrips, loopers, silverfish, beetles, borers, weevils, fruitworms, rootworms, wireworms, mealworms, flies, maggots, gnats, fleeceworms, screwworms, midges, aphids, leafhoppers, bees, wasps, ants, cutworms, bollworms, leafcutters, caterpillars, budworms, hornworms, grasshoppers, crickets, moths, roaches, mosquitoes, armyworms, millipedes and sowbugs, a molluscicide such that the composition can be utilized to control slugs and snails, an oral vaccine, such as a rabies vaccine, such that the composition is useful in the vaccination of wild animals, for example raccoons, skunks, mongoose, feral dogs and foxes and an oral contraceptive, such as a contraceptive for controlling the deer population.

Test A

The slug formulations of Examples 15 to 19 were compared with two commercially available pellet products, Draza (Bayer UK) and PP Minipellets (ICI Plant Protection), under field conditions. Three of the formulations of this invention were as effective as the commercial standards. Two of the formulations of this invention were more effective than the commercial standards.

| Materials Tested |
|---|
| Commercial standards: |
| Draza pellets (Bayer UK) 4% methiocarb. |
| PP Minipellets (ICI Plant Protection) 6% metaldehyde. |
| Formulations of the Invention: |

| | |
|---|---|
| Example 15 | 0.5% methomyl |
| Example 16 | 0.5% methomyl |
| Example 17 | 0.5% methomyl |
| Example 18 | 5.0% methiocarb |
| Example 19 | 5.0% methiocarb |

The experiment was laid out on an established grass sward, resown four years before, and still predominantly perennial ryegrass, with some invasion especially by Poa spp. and some broad-leaved weeds. Pre-treatment trapping confirmed the presence of the major pest species *Deroceras reticulatum* (Muller) (Grey Field Slug), in all stages from <100mg to >1000mg, plus *Arion hortensis* Ferussac and *Arion intermedius* Normand, predominantly as mature individuals.

The seven formulations were compared by establishing 0.5m² bait stations at 10 m intervals across the field. The grass was closely mowed on these areas to facilitate visual examination and covered by simple galvanized wire-mesh cages to prevent removal of pellets or poisoned slugs by birds and small mammals.

The recommended rate of application of the most widely used commercial formulation 'Draza' (Bayer UK) is 5.5 kg/ha (0.5 g/m²). Each 0.5 m² station had a theoretical recruitment area of 78 m2 surrounding it. Each 0.5 m² station was therefore treated with enough formulation for this 78 m² area at a rate of 5.5 kg/ha, i.e. 39 g. This ensured that adequate formulation was present to achieve maximum kill.

Twenty-eight stations were laid out on a grid at 10 m intervals in four randomized blocks of cover treatments.

Following treatment each station was examined every morning for poisoned slugs, dead or immobilized on the grass surface, daily for 20 days, then at longer intervals until day 32, when cold weather terminated surface activity. Poisoned slugs were collected, identified and held in high humidity with food for a further 7-10 days until they died or resumed normal activity. Plastic Petri dishes floored with wet filter paper and with carrot as food were used as recovery chambers. These were kept at ambient temperature.

Cumulative totals of all slugs collected over the first 20-day period of the experiment were compared by analysis of variance, and mean numbers 'caught' calculated for the seven formulations tested.

A grand total of 90 slugs, all species, were collected during the intial 20-day period from all stations. This is a relatively small number, and reflects a low local population level rather than weather unfavorable for surface activity, as much higher numbers were simultaneously recorded on nearby irrigated prepared sites. Raw data are presented in Table 1. Nevertheless, all the formulations tested poisoned slugs, and analysis of variance showed there were significant differences between treatments at the 5% probability level (Table 2). The mean values in Table 2 suggest that three of the formulations of the invention, Examples 15 to 17, were as effective as products Draza (4% methiocarb) and PP Mini Pellets (6% metaldehyde), and that the remaining two, Examples 18 and 19, were more effective.

Sub-lethal poisoning which immobilizes slugs on the surface, but allows recovery under damp conditions, is known to adversely affect the field performance of currently commercially available formulations, especially metaldehyde-based ones. This is confirmed in the recovery values obtained here (Table 3), where 64% recovery was noted with PP Mini Pellets and 46% recovery with Draza pellets. The formulations of Examples 15 to 17 were as poor or worse than the metaldehyde-based commercial formulation in this respect, but the formulations of Examples 18 and 19 gave the lowest recovery rates of all, at 32 and 38%, respectively.

Slugs poisoned by the formulations of Examples 15 to 19 had a flaccid appearance and remained paralyzed for days before either succumbing or recovering, closely resembling slugs poisoned by the carbamate methiocarb in this respect.

There was no obvious difference in the susceptibility of the three slug species present to any of the formulations, but numbers were too low to detect any differences that were not absolute.

The formulations of Examples 15 to 19 retained their physical integrity as well as Draza pellets, and better than PP Mini Pellets, and were still intact after 32 days, which included several spells of prolonged heavy rain. Mold growth was observed on the experimental formulations from day 10 onward, and appeared to be worse on the three 0.5% active ingredient formulations: none was observed on the Draza pellets at this time. Between day 20 and day 32 only a further three slugs were caught, but this apparent fall in pellet effectiveness was confounded with weather unfavorable for surface activity, affected all formulations equally.

All of the formulations of Examples 15 to 19 killed non-target species. Dead earthworms, Lumbrious spp., were observed on areas treated with Draza pellets and the formulations of Examples 15 to 19, but not on areas treated with metaldehyde-based PP Mini Pellets. Dead carabid beetles, Pterostichus spp., were noted on plots treated with Draza, and the formulations of Examples 15 and 19. A single paralyzed cutworm larva (Noctuidae, Agrotis sp.) was found on a plot treated with the formulation of Example 17.

TABLE 1

| | | | | | | | | | | | | | |
|---|---|---|---|---|---|---|---|---|---|---|---|---|---|
| DAILY "CATCH", ALL SPP., OVER 20-DAY PERIOD | | | | | | | | | | | | | |
| | | Plot No. | +1 day | +2 day | +3 day | +4 day | +5 day | +6 day | +7 day | +8 day | +9 day | +10 day | +11 day |
| 1. Methiocarb. 4% "Draza" | | 3 | | | | | | | | | | | |
| | | 11 | 1 | | | | 1 | | | | | | |
| | | 15 | | 2 | | | | 1 | | | | | |
| | | 27 | | | | 1 | | | | | | 1 | |
| | | | 1 | 2 | 0 | 1 | 1 | 1 | 0 | 0 | 0 | 1 | 0 |
| 2. Metaldehyde 6% PP Mini-pellets | | 6 | | | | | | | | | | | |
| | | 8 | | | 1 | | | | | | | | |
| | | 19 | 1 | 1 | | | 1 | | 1 | | | | |
| | | 28 | | | | | 1 | | | | | | |
| | | | 1 | 1 | 1 | 0 | 2 | 0 | 1 | 0 | 0 | 0 | 0 |
| 3. Example 15 0.5% | | 4 | | | | | 1 | | | | | | |
| | | 9 | | | | | | | | | | | 1 |
| | | 18 | | | | | | | | | | | |
| | | 22 | | | | | | | 1 | | | | |
| | | | 0 | 0 | 0 | 0 | 1 | 0 | 1 | 0 | 0 | 0 | 1 |
| 4. Example 16 0.5% | | 1 | | | | | | | | | | | 1 |
| | | 13 | 1 | | | | 1 | | | | | | |
| | | 16 | | | | | 1 | | | | | 1 | |
| | | 25 | | 1 | 1 | | 1 | | | | | | |
| | | | 1 | 1 | 1 | 0 | 3 | 0 | 0 | 0 | 0 | 1 | 1 |
| 5. Example 17 0.5% | | 5 | | | 1 | | | | | | | | |
| | | 14 | | 2 | | | | | | | | 1 | |
| | | 17 | | | 1 | | 1 | | | | | | |
| | | 26 | | 2 | | | | | | | | | |
| | | | 0 | 4 | 2 | 0 | 1 | 0 | 0 | 0 | 0 | 1 | 0 |
| 6. Example 18 | | 2 | | | | 1 | 1 | | | | | | |
| | | 10 | | | 1 | | 1 | | | | | | |
| | | 20 | | | | 2 | | | | | | 2 | 1 |
| | | 24 | | | 1 | | | | | | | | |
| | | | 0 | 0 | 2 | 3 | 3 | 0 | 0 | 0 | 0 | 2 | 1 |
| 7. Example 19 | | 7 | | | | | 1 | | | | | | 1 |
| | | 12 | 1 | | | | | | | | | | |
| | | 21 | | | | | 1 | | 1 | | | 2 | 1 |
| | | 23 | | 1 | 1 | | | | 2 | | | | |
| | | | 1 | 1 | 1 | 0 | 2 | 0 | 3 | 0 | 0 | 2 | 2 |
| TOTAL DAILY "CATCH" | | | 4 | 9 | 7 | 4 | 13 | 1 | 5 | 1 | 0 | 6 | 6 |

TABLE 1-continued

DAILY "CATCH", ALL SPP., OVER 20-DAY PERIOD

|  | Plot No. | +12 day | +13 day | +14 day | +15 day | +16 day | +17 day | +18 day | +19 day | +20 day | Total at +20 days |
|---|---|---|---|---|---|---|---|---|---|---|---|
| 1. Methiocarb. 4% "Draza" | 3 |  |  |  |  |  | 1 |  |  |  | 1 |
|  | 11 | 1 |  |  | 2 |  |  |  | 1 |  | 6 |
|  | 15 |  |  |  |  |  |  |  |  |  | 3 |
|  | 27 |  |  |  |  |  | 1 |  |  |  | 3 |
|  |  | 1 | 0 | 0 | 2 | 0 | 2 | 0 | 1 | 0 | 13 |
| 2. Metaldehyde 6% PP Mini-pellets | 6 |  | 1 |  |  |  |  |  |  |  | 1 |
|  | 8 |  |  |  |  | 1 | 1 |  |  |  | 3 |
|  | 19 |  |  |  |  |  |  |  |  |  | 4 |
|  | 28 |  | 1 |  |  | 1 |  |  |  |  | 3 |
|  |  | 0 | 2 | 0 | 0 | 2 | 1 | 0 | 0 | 0 | 11 |
| 3. Example 15 0.5% | 4 |  |  |  |  |  |  |  |  |  | 1 |
|  | 9 |  | 3 |  | 1 |  |  |  |  |  | 5 |
|  | 18 |  |  |  |  |  |  |  |  |  | 0 |
|  | 22 |  |  |  |  |  | 1 |  |  |  | 2 |
|  |  | 0 | 3 | 0 | 1 | 0 | 1 | 0 | 0 | 0 | 8 |
| 4. Example 16 0.5% | 1 |  |  |  |  |  |  |  |  |  | 1 |
|  | 13 |  | 1 |  | 1 |  |  |  |  |  | 5 |
|  | 16 |  |  |  |  |  |  |  |  |  | 2 |
|  | 25 |  |  |  |  |  |  | 1 |  |  | 4 |
|  |  | 0 | 1 | 0 | 1 | 0 | 0 | 1 | 0 | 0 | 12 |
| 5. Example 17 0.5% | 5 |  |  |  |  |  |  |  |  |  | 1 |
|  | 14 |  |  |  |  |  |  |  |  |  | 3 |
|  | 17 |  |  |  |  |  |  |  |  |  | 2 |
|  | 26 |  |  |  |  |  |  |  |  |  | 2 |
|  |  | 0 | 0 | 0 | 0 | 0 | 0 | 0 | 0 | 0 | 8 |
| 6. Example 18 | 2 | 1 |  |  |  |  |  |  |  |  | 3 |
|  | 10 |  |  |  | 1 |  |  |  |  |  | 4 |
|  | 20 | 2 |  |  |  |  |  |  |  |  | 7 |
|  | 24 |  |  |  |  | 1 |  |  |  |  | 2 |
|  |  | 3 | 0 | 0 | 1 | 1 | 0 | 0 | 0 | 0 | 16 |
| 7. Example 19 | 7 | 1 |  |  | 1 |  |  |  |  |  | 4 |
|  | 12 |  | 1 |  | 2 | 1 |  |  |  |  | 5 |
|  | 21 |  |  |  | 1 |  |  |  |  |  | 6 |
|  | 23 |  |  |  | 2 |  |  |  | 1 |  | 7 |
|  |  | 1 | 1 | 0 | 5 | 1 | 1 | 1 | 0 | 0 | 22 |
| TOTAL DAILY "CATCH" |  | 4 | 8 | 0 | 10 | 4 | 5 | 2 | 1 | 0 | 90 |

TABLE 2

Mean numbers of slugs "caught" over 20-day period (all spp.), and analysis of variance.

| Formulation | n caught/0.5 m$^2$ | SED |
|---|---|---|
| Draza | 2.00 | 1.011 |
| PP Minipellets | 2.75 |  |
| Example 15 | 2.00 |  |
| Example 16 | 3.00 |  |
| Example 17 | 2.00 |  |
| Example 18 | 4.00 |  |
| Example 19 | 5.50 |  |

| Variation | d.f. | s.s | m.s. | variance ratio |
|---|---|---|---|---|
| Block | 3 | 16.964 | 5.655 |  |
| Treatment | 6 | 41.214 | 6.869 | 3.36 (required vr @ 5¼, 2.66) |
| Residual | 18 | 36.786 | 2.044 |  |

TABLE 3

| Formulation | Proportion of immobilized slugs which recovered (all spp.) | |
|---|---|---|
|  | No. slugs "caught" | No. "recovered" (%) |
| Draza | 13 | 46 |
| PP Mini Pellets | 11 | 64 |
| Example 15 | 8 | 75 |
| Example 16 | 12 | 75 |
| Example 17 | 8 | 68 |
| Example 18 | 16 | 32 |
| Example 19 | 22 | 38 |

What is claimed is:

1. A method for controlling pests comprising applying to the habitat of the pest a palatable pesticidal composition in solid form comprising, based on the total composition,
   (a) 0.5 to 33 weight % of ethylene and vinyl acetate copolymer with from 18 to 50 weight % vinyl acetate,
   (b) 0.001–10 weight % of a bioactive agent, and
   (c) 67–99 weight % of a protein and carbohydrate and lipid source providing the remaining weight wherein the pest is a vertebrate.

* * * * *